United States Patent
Zhan (10) Patent No.: US 10,507,022 B2
(45) Date of Patent: Dec. 17, 2019

(54) SURGICAL STAPLING APPARATUS (71) Applicant: Covidien LP, Mansfield, MA (US)

(72) Inventor: Hui Zhan, Shanghai (CN)

(73) Assignee: Covidien LP, Mansfield, MA (US)

( * ) Notice: Subject to any disclaimer, the term of this patent is extended or adjusted under 35 U.S.C. 154(b) by 346 days.

(21) Appl. No.: 15/316,527

(22) PCT Filed: Jun. 12, 2014

(86) PCT No.: PCT/CN2014/079738
§ 371 (c)(1),
(2) Date: Dec. 6, 2016

(87) PCT Pub. No.: WO2015/188347
PCT Pub. Date: Dec. 17, 2015

(65) Prior Publication Data
US 2017/0156730 A1 Jun. 8, 2017

(51) Int. Cl.
*A61B 17/115* (2006.01)
*A61B 17/072* (2006.01)
*A61B 90/00* (2016.01)

(52) U.S. Cl.
CPC ... *A61B 17/1155* (2013.01); *A61B 2017/0725* (2013.01); *A61B 2090/0811* (2016.02)

(58) Field of Classification Search
None
See application file for complete search history.

(56) References Cited

U.S. PATENT DOCUMENTS

| 3,193,165 A | 7/1965 | Akhalaya et al. |
| 3,388,847 A | 6/1968 | Kasulin et al. |
| 3,552,626 A | 1/1971 | Astafiev et al. |
| 3,638,652 A | 2/1972 | Kelley |
| 3,771,526 A | 11/1973 | Rudie |
| 4,198,982 A | 4/1980 | Fortner et al. |

(Continued)

FOREIGN PATENT DOCUMENTS

| CA | 908529 A | 8/1972 |
| CA | 2805365 A1 | 8/2013 |

(Continued)

OTHER PUBLICATIONS

Japanese Office Action dated Mar. 14, 2018, issued in JP Appln. No. 2016572269.

(Continued)

*Primary Examiner* — Hemant Desai
*Assistant Examiner* — Amelia Jae-Ippel Vorce (57) ABSTRACT

A surgical stapling apparatus (10) having an adjustable minimum tissue gap (G) is provided. The surgical stapling apparatus (10) includes a proximal handle portion (20), an elongated central body portion (30), a distal head portion (40), an anvil assembly (50), and an approximation assembly (100). The approximation assembly (100) includes a drive screw (140), a screw stop (150), and a screw extension (160). The adjustable minimum tissue gap (G) can be adjusted by selectively securing the screw extension (160) to the drive screw (140) using a first or second pair of openings (145, 147) of the drive screw (140). A method is also provided to determine the minimum tissue gap (G) of the surgical stapling apparatus (10).

20 Claims, 4 Drawing Sheets

(56) References Cited

U.S. PATENT DOCUMENTS

| | | |
|---|---|---|
| 4,207,898 A | 6/1980 | Becht |
| 4,289,133 A | 9/1981 | Rothfuss |
| 4,304,236 A | 12/1981 | Conta et al. |
| 4,319,576 A | 3/1982 | Rothfuss |
| 4,350,160 A | 9/1982 | Kolesov et al. |
| 4,351,466 A | 9/1982 | Noiles |
| 4,379,457 A | 4/1983 | Gravener et al. |
| 4,473,077 A | 9/1984 | Noiles et al. |
| 4,476,863 A | 10/1984 | Kanshin et al. |
| 4,485,817 A | 12/1984 | Swiggett |
| 4,488,523 A | 12/1984 | Shichman |
| 4,505,272 A | 3/1985 | Utyamyshev et al. |
| 4,505,414 A | 3/1985 | Filipi |
| 4,520,817 A | 6/1985 | Green |
| 4,550,870 A | 11/1985 | Krumme et al. |
| 4,573,468 A | 3/1986 | Conta et al. |
| 4,576,167 A | 3/1986 | Noiles |
| 4,592,354 A | 6/1986 | Rothfuss |
| 4,603,693 A | 8/1986 | Conta et al. |
| 4,606,343 A | 8/1986 | Conta et al. |
| 4,632,290 A | 12/1986 | Green et al. |
| 4,646,745 A | 3/1987 | Noiles |
| 4,665,917 A | 5/1987 | Clanton et al. |
| 4,667,673 A | 5/1987 | Li |
| 4,671,445 A | 6/1987 | Barker et al. |
| 4,700,703 A | 10/1987 | Resnick et al. |
| 4,703,887 A | 11/1987 | Clanton et al. |
| 4,708,141 A | 11/1987 | Inoue et al. |
| 4,717,063 A | 1/1988 | Ebihara |
| 4,752,024 A | 6/1988 | Green et al. |
| 4,754,909 A | 7/1988 | Barker et al. |
| 4,776,506 A | 10/1988 | Green |
| 4,817,847 A | 4/1989 | Redtenbacher et al. |
| 4,873,977 A | 10/1989 | Avant et al. |
| 4,893,662 A | 1/1990 | Gervasi |
| 4,903,697 A | 2/1990 | Resnick et al. |
| 4,907,591 A | 3/1990 | Vasconcellos et al. |
| 4,917,114 A | 4/1990 | Green et al. |
| 4,957,499 A | 9/1990 | Lipatov et al. |
| 4,962,877 A | 10/1990 | Hervas |
| 5,005,749 A | 4/1991 | Aranyi |
| 5,042,707 A | 8/1991 | Taheri |
| 5,047,039 A | 9/1991 | Avant et al. |
| 5,104,025 A | 4/1992 | Main et al. |
| 5,119,983 A | 6/1992 | Green et al. |
| 5,122,156 A | 6/1992 | Granger et al. |
| 5,139,513 A | 8/1992 | Segato |
| 5,158,222 A | 10/1992 | Green et al. |
| 5,188,638 A | 2/1993 | Tzakis |
| 5,193,731 A | 3/1993 | Aranyi |
| 5,197,648 A | 3/1993 | Gingold |
| 5,197,649 A | 3/1993 | Bessler et al. |
| 5,205,459 A | 4/1993 | Brinkerhoff et al. |
| 5,221,036 A | 6/1993 | Takase |
| 5,222,963 A | 6/1993 | Brinkerhoff et al. |
| 5,253,793 A | 10/1993 | Green et al. |
| 5,261,920 A | 11/1993 | Main et al. |
| 5,271,543 A | 12/1993 | Grant et al. |
| 5,271,544 A | 12/1993 | Fox et al. |
| 5,275,322 A | 1/1994 | Brinkerhoff et al. |
| 5,282,810 A | 2/1994 | Allen et al. |
| 5,285,944 A | 2/1994 | Green et al. |
| 5,285,945 A | 2/1994 | Brinkerhoff et al. |
| 5,292,053 A | 3/1994 | Bilotti et al. |
| 5,309,927 A | 5/1994 | Welch |
| 5,312,024 A | 5/1994 | Grant et al. |
| 5,314,435 A | 5/1994 | Green et al. |
| 5,314,436 A | 5/1994 | Wilk |
| 5,330,486 A | 7/1994 | Wilk |
| 5,333,773 A | 8/1994 | Main et al. |
| 5,344,059 A | 9/1994 | Green et al. |
| 5,346,115 A | 9/1994 | Perouse et al. |
| 5,348,259 A | 9/1994 | Blanco et al. |
| 5,350,104 A | 9/1994 | Main et al. |
| 5,355,897 A | 10/1994 | Pietrafitta et al. |
| 5,360,154 A | 11/1994 | Green |
| 5,368,215 A | 11/1994 | Green et al. |
| 5,392,979 A | 2/1995 | Green et al. |
| 5,395,030 A | 3/1995 | Kuramoto et al. |
| 5,403,333 A | 4/1995 | Kaster et al. |
| 5,404,870 A | 4/1995 | Brinkerhoff et al. |
| 5,411,508 A | 5/1995 | Bessler et al. |
| 5,425,738 A | 6/1995 | Gustafson et al. |
| 5,433,721 A | 7/1995 | Hooven et al. |
| 5,437,684 A | 8/1995 | Calabrese et al. |
| 5,439,156 A | 8/1995 | Grant et al. |
| 5,443,198 A | 8/1995 | Viola et al. |
| 5,447,514 A | 9/1995 | Gerry et al. |
| 5,454,825 A | 10/1995 | Van Leeuwen et al. |
| 5,464,415 A | 11/1995 | Chen |
| 5,470,006 A | 11/1995 | Rodak |
| 5,474,223 A | 12/1995 | Viola et al. |
| 5,497,934 A | 3/1996 | Brady et al. |
| 5,503,635 A | 4/1996 | Sauer et al. |
| 5,522,534 A | 6/1996 | Viola et al. |
| 5,533,661 A | 7/1996 | Main et al. |
| 5,588,579 A | 12/1996 | Schnut et al. |
| 5,609,285 A | 3/1997 | Grant et al. |
| 5,626,591 A | 5/1997 | Kockerling et al. |
| 5,632,433 A | 5/1997 | Grant et al. |
| 5,639,008 A | 6/1997 | Gallagher et al. |
| 5,641,111 A | 6/1997 | Ahrens et al. |
| 5,658,300 A | 8/1997 | Bito et al. |
| 5,669,918 A | 9/1997 | Balazs et al. |
| 5,685,474 A | 11/1997 | Seeber |
| 5,709,335 A | 1/1998 | Heck |
| 5,715,987 A | 2/1998 | Kelley et al. |
| 5,718,360 A | 2/1998 | Green et al. |
| 5,720,755 A | 2/1998 | Dakov |
| 5,732,872 A | 3/1998 | Bolduc et al. |
| 5,749,896 A | 5/1998 | Cook |
| 5,758,814 A | 6/1998 | Gallagher et al. |
| 5,799,857 A | 9/1998 | Robertson et al. |
| 5,814,055 A | 9/1998 | Knodel et al. |
| 5,833,698 A | 11/1998 | Hinchliffe et al. |
| 5,836,503 A | 11/1998 | Ehrenfels et al. |
| 5,839,639 A | 11/1998 | Sauer et al. |
| 5,855,312 A | 1/1999 | Toledano |
| 5,860,581 A | 1/1999 | Robertson et al. |
| 5,868,760 A | 2/1999 | McGuckin, Jr. |
| 5,881,943 A | 3/1999 | Heck et al. |
| 5,915,616 A | 6/1999 | Viola et al. |
| 5,947,363 A | 9/1999 | Bolduc et al. |
| 5,951,576 A | 9/1999 | Wakabayashi |
| 5,957,363 A | 9/1999 | Heck |
| 5,993,468 A | 11/1999 | Rygaard |
| 6,024,748 A | 2/2000 | Manzo et al. |
| 6,050,472 A | 4/2000 | Shibata |
| 6,053,390 A | 4/2000 | Green et al. |
| 6,068,636 A | 5/2000 | Chen |
| 6,083,241 A | 7/2000 | Longo et al. |
| 6,102,271 A | 8/2000 | Longo et al. |
| 6,117,148 A | 9/2000 | Ravo et al. |
| 6,119,913 A | 9/2000 | Adams et al. |
| 6,126,058 A | 10/2000 | Adams et al. |
| 6,142,933 A | 11/2000 | Longo et al. |
| 6,149,667 A | 11/2000 | Hovland et al. |
| 6,176,413 B1 | 1/2001 | Heck et al. |
| 6,179,195 B1 | 1/2001 | Adams et al. |
| 6,193,129 B1 | 2/2001 | Bittner et al. |
| 6,203,553 B1 | 3/2001 | Robertson et al. |
| 6,209,773 B1 | 4/2001 | Bolduc et al. |
| 6,241,140 B1 | 6/2001 | Adams et al. |
| 6,253,984 B1 | 7/2001 | Heck et al. |
| 6,258,107 B1 | 7/2001 | Balazs et al. |
| 6,264,086 B1 | 7/2001 | McGuckin, Jr. |
| 6,269,997 B1 | 8/2001 | Balazs et al. |
| 6,273,897 B1 | 8/2001 | Dalessandro et al. |
| 6,279,809 B1 | 8/2001 | Nicolo |
| 6,302,311 B1 | 10/2001 | Adams et al. |
| 6,338,737 B1 | 1/2002 | Toledano |
| 6,343,731 B1 | 2/2002 | Adams et al. |
| 6,387,105 B1 | 5/2002 | Gifford, III et al. |
| 6,398,795 B1 | 6/2002 | McAlister et al. |

(56) References Cited

U.S. PATENT DOCUMENTS

| | | |
|---|---|---|
| 6,402,008 B1 | 6/2002 | Lucas |
| 6,439,446 B1 | 8/2002 | Perry et al. |
| 6,443,973 B1 | 9/2002 | Whitman |
| 6,450,390 B2 | 9/2002 | Heck et al. |
| 6,478,210 B2 | 11/2002 | Adams et al. |
| 6,488,197 B1 | 12/2002 | Whitman |
| 6,491,201 B1 | 12/2002 | Whitman |
| 6,494,877 B2 | 12/2002 | Odell et al. |
| 6,503,259 B2 | 1/2003 | Huxel et al. |
| 6,517,566 B1 | 2/2003 | Hovland et al. |
| 6,520,398 B2 | 2/2003 | Nicolo |
| 6,533,157 B1 | 3/2003 | Whitman |
| 6,551,334 B2 | 4/2003 | Blatter et al. |
| 6,578,751 B2 | 6/2003 | Hartwick |
| 6,585,144 B2 | 7/2003 | Adams et al. |
| 6,588,643 B2 | 7/2003 | Bolduc et al. |
| 6,592,596 B1 | 7/2003 | Geitz |
| 6,601,749 B2 | 8/2003 | Sullivan et al. |
| 6,605,078 B2 | 8/2003 | Adams |
| 6,605,098 B2 | 8/2003 | Nobis et al. |
| 6,626,921 B2 | 9/2003 | Blatter et al. |
| 6,629,630 B2 | 10/2003 | Adams |
| 6,631,837 B1 | 10/2003 | Heck |
| 6,632,227 B2 | 10/2003 | Adams |
| 6,632,237 B2 | 10/2003 | Ben-David et al. |
| 6,652,542 B2 | 11/2003 | Blatter et al. |
| 6,659,327 B2 | 12/2003 | Heck et al. |
| 6,676,671 B2 | 1/2004 | Robertson et al. |
| 6,681,979 B2 | 1/2004 | Whitman |
| 6,685,079 B2 | 2/2004 | Sharma et al. |
| 6,695,198 B2 | 2/2004 | Adams et al. |
| 6,695,199 B2 | 2/2004 | Whitman |
| 6,698,643 B2 | 3/2004 | Whitman |
| 6,716,222 B2 | 4/2004 | McAlister et al. |
| 6,716,233 B1 | 4/2004 | Whitman |
| 6,726,697 B2 | 4/2004 | Nicholas et al. |
| 6,742,692 B2 | 6/2004 | Hartwick |
| 6,743,244 B2 | 6/2004 | Blatter et al. |
| 6,763,993 B2 | 7/2004 | Bolduc et al. |
| 6,769,590 B2 | 8/2004 | Vresh et al. |
| 6,769,594 B2 | 8/2004 | Orban, III |
| 6,820,791 B2 | 11/2004 | Adams |
| 6,821,282 B2 | 11/2004 | Perry et al. |
| 6,827,246 B2 | 12/2004 | Sullivan et al. |
| 6,840,423 B2 | 1/2005 | Adams et al. |
| 6,843,403 B2 | 1/2005 | Whitman |
| 6,846,308 B2 | 1/2005 | Whitman et al. |
| 6,852,122 B2 | 2/2005 | Rush |
| 6,866,178 B2 | 3/2005 | Adams et al. |
| 6,872,214 B2 | 3/2005 | Sonnenschein et al. |
| 6,874,669 B2 | 4/2005 | Adams et al. |
| 6,884,250 B2 | 4/2005 | Monassevitch et al. |
| 6,905,504 B1 | 6/2005 | Vargas |
| 6,938,814 B2 | 9/2005 | Sharma et al. |
| 6,942,675 B1 | 9/2005 | Vargas |
| 6,945,444 B2 | 9/2005 | Gresham et al. |
| 6,953,138 B1 | 10/2005 | Dworak et al. |
| 6,957,758 B2 | 10/2005 | Aranyi |
| 6,959,851 B2 | 11/2005 | Heinrich |
| 6,978,922 B2 | 12/2005 | Bilotti et al. |
| 6,981,941 B2 | 1/2006 | Whitman et al. |
| 6,981,979 B2 | 1/2006 | Nicolo |
| 7,032,798 B2 | 4/2006 | Whitman et al. |
| 7,059,331 B2 | 6/2006 | Adams et al. |
| 7,059,510 B2 | 6/2006 | Orban, III |
| 7,077,856 B2 | 7/2006 | Whitman |
| 7,080,769 B2 | 7/2006 | Vresh et al. |
| 7,086,267 B2 | 8/2006 | Dworak et al. |
| 7,114,642 B2 | 10/2006 | Whitman |
| 7,118,528 B1 | 10/2006 | Piskun |
| 7,122,044 B2 | 10/2006 | Bolduc et al. |
| 7,128,748 B2 | 10/2006 | Mooradian et al. |
| 7,141,055 B2 | 11/2006 | Abrams et al. |
| 7,168,604 B2 | 1/2007 | Milliman et al. |
| 7,179,267 B2 | 2/2007 | Nolan et al. |
| 7,182,239 B1 | 2/2007 | Myers |
| 7,195,142 B2 | 3/2007 | Orban, III |
| 7,207,168 B2 | 4/2007 | Doepker et al. |
| 7,220,237 B2 | 5/2007 | Gannoe et al. |
| 7,234,624 B2 | 6/2007 | Gresham et al. |
| 7,235,089 B1 | 6/2007 | McGuckin, Jr. |
| RE39,841 E | 9/2007 | Bilotti et al. |
| 7,285,125 B2 | 10/2007 | Viola |
| 7,303,106 B2 | 12/2007 | Milliman et al. |
| 7,303,107 B2 | 12/2007 | Milliman et al. |
| 7,309,341 B2 | 12/2007 | Ortiz et al. |
| 7,322,994 B2 | 1/2008 | Nicholas et al. |
| 7,325,713 B2 | 2/2008 | Aranyi |
| 7,334,718 B2 | 2/2008 | McAlister et al. |
| 7,335,212 B2 | 2/2008 | Edoga et al. |
| 7,364,060 B2 | 4/2008 | Milliman |
| 7,398,908 B2 | 7/2008 | Holsten et al. |
| 7,399,305 B2 | 7/2008 | Csiky et al. |
| 7,401,721 B2 | 7/2008 | Holsten et al. |
| 7,401,722 B2 | 7/2008 | Hur |
| 7,407,075 B2 | 8/2008 | Holsten et al. |
| 7,410,086 B2 | 8/2008 | Ortiz et al. |
| 7,422,137 B2 | 9/2008 | Manzo |
| 7,422,138 B2 | 9/2008 | Bilotti et al. |
| 7,431,191 B2 | 10/2008 | Milliman |
| 7,438,718 B2 | 10/2008 | Milliman et al. |
| 7,455,676 B2 | 11/2008 | Holsten et al. |
| 7,455,682 B2 | 11/2008 | Viola |
| 7,481,347 B2 | 1/2009 | Roy |
| 7,494,038 B2 | 2/2009 | Milliman |
| 7,506,791 B2 | 3/2009 | Omaits et al. |
| 7,516,877 B2 | 4/2009 | Aranyi |
| 7,527,185 B2 | 5/2009 | Harari et al. |
| 7,537,602 B2 | 5/2009 | Whitman |
| 7,540,839 B2 | 6/2009 | Butler et al. |
| 7,546,939 B2 | 6/2009 | Adams et al. |
| 7,546,940 B2 | 6/2009 | Milliman et al. |
| 7,547,312 B2 | 6/2009 | Bauman et al. |
| 7,556,186 B2 | 7/2009 | Milliman |
| 7,559,451 B2 | 7/2009 | Sharma |
| 7,585,306 B2 | 9/2009 | Abbott et al. |
| 7,588,174 B2 | 9/2009 | Holsten et al. |
| 7,600,663 B2 | 10/2009 | Green |
| 7,611,038 B2 | 11/2009 | Racenet et al. |
| 7,635,385 B2 | 12/2009 | Milliman et al. |
| 7,669,747 B2 | 3/2010 | Weisenburgh, II et al. |
| 7,686,201 B2 | 3/2010 | Csiky |
| 7,694,864 B2 | 4/2010 | Okada et al. |
| 7,699,204 B2 | 4/2010 | Viola |
| 7,708,181 B2 | 5/2010 | Cole et al. |
| 7,717,313 B2 | 5/2010 | Criscuolo et al. |
| 7,721,932 B2 | 5/2010 | Cole et al. |
| 7,726,539 B2 | 6/2010 | Holsten et al. |
| 7,743,958 B2 | 6/2010 | Orban, III |
| 7,744,627 B2 | 6/2010 | Orban, III et al. |
| 7,770,776 B2 | 8/2010 | Chen et al. |
| 7,771,440 B2 | 8/2010 | Ortiz et al. |
| 7,776,060 B2 | 8/2010 | Mooradian et al. |
| 7,793,813 B2 | 9/2010 | Bettuchi |
| 7,802,712 B2 | 9/2010 | Milliman et al. |
| 7,823,592 B2 | 11/2010 | Bettuchi et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,845,536 B2 | 12/2010 | Viola et al. |
| 7,845,538 B2 | 12/2010 | Whitman |
| 7,857,187 B2 | 12/2010 | Milliman |
| 7,886,951 B2 | 2/2011 | Hessler |
| 7,896,215 B2 | 3/2011 | Adams et al. |
| 7,900,806 B2 | 3/2011 | Chen et al. |
| 7,909,039 B2 | 3/2011 | Hur |
| 7,909,219 B2 | 3/2011 | Cole et al. |
| 7,909,222 B2 | 3/2011 | Cole et al. |
| 7,909,223 B2 | 3/2011 | Cole et al. |
| 7,913,892 B2 | 3/2011 | Cole et al. |
| 7,918,377 B2 | 4/2011 | Measamer et al. |
| 7,922,062 B2 | 4/2011 | Cole et al. |
| 7,922,743 B2 | 4/2011 | Heinrich et al. |
| 7,931,183 B2 | 4/2011 | Orban, III |

(56) References Cited

U.S. PATENT DOCUMENTS

| | | |
|---|---|---|
| 7,938,307 B2 | 5/2011 | Bettuchi |
| 7,942,302 B2 | 5/2011 | Roby et al. |
| 7,951,166 B2 | 5/2011 | Orban, III et al. |
| 7,959,050 B2 | 6/2011 | Smith et al. |
| 7,967,181 B2 | 6/2011 | Viola et al. |
| 7,975,895 B2 | 7/2011 | Milliman |
| 8,002,795 B2 | 8/2011 | Beetel |
| 8,006,701 B2 | 8/2011 | Bilotti et al. |
| 8,006,889 B2 | 8/2011 | Adams et al. |
| 8,011,551 B2 | 9/2011 | Marczyk et al. |
| 8,011,554 B2 * | 9/2011 | Milliman ............ A61B 17/115 227/175.1 |
| 8,016,177 B2 | 9/2011 | Bettuchi et al. |
| 8,016,858 B2 | 9/2011 | Whitman |
| 8,020,741 B2 | 9/2011 | Cole et al. |
| 8,025,199 B2 | 9/2011 | Whitman et al. |
| 8,028,885 B2 | 10/2011 | Smith et al. |
| 8,038,046 B2 | 10/2011 | Smith et al. |
| 8,043,207 B2 | 10/2011 | Adams |
| 8,066,167 B2 | 11/2011 | Measamer et al. |
| 8,066,169 B2 | 11/2011 | Viola |
| 8,070,035 B2 | 12/2011 | Holsten et al. |
| 8,070,037 B2 | 12/2011 | Csiky |
| 8,096,458 B2 | 1/2012 | Hessler |
| 8,109,426 B2 | 2/2012 | Milliman et al. |
| 8,109,427 B2 | 2/2012 | Orban, III |
| 8,113,406 B2 | 2/2012 | Holsten et al. |
| 8,113,407 B2 | 2/2012 | Holsten et al. |
| 8,123,103 B2 | 2/2012 | Milliman |
| 8,128,645 B2 | 3/2012 | Sonnenschein et al. |
| 8,132,703 B2 | 3/2012 | Milliman et al. |
| 8,136,712 B2 | 3/2012 | Zingman |
| 8,146,790 B2 | 4/2012 | Milliman |
| 8,146,791 B2 | 4/2012 | Bettuchi et al. |
| 8,181,838 B2 | 5/2012 | Milliman et al. |
| 8,192,460 B2 | 6/2012 | Orban, III et al. |
| 8,201,720 B2 | 6/2012 | Hessler |
| 8,203,782 B2 | 6/2012 | Brueck et al. |
| 8,211,130 B2 | 7/2012 | Viola |
| 8,225,799 B2 | 7/2012 | Bettuchi |
| 8,225,981 B2 | 7/2012 | Criscuolo et al. |
| 8,231,041 B2 | 7/2012 | Marczyk et al. |
| 8,231,042 B2 | 7/2012 | Hessler et al. |
| 8,257,391 B2 | 9/2012 | Orban, III et al. |
| 8,267,301 B2 | 9/2012 | Milliman et al. |
| 8,272,552 B2 | 9/2012 | Holsten et al. |
| 8,276,802 B2 | 10/2012 | Kostrzewski |
| 8,281,975 B2 | 10/2012 | Criscuolo et al. |
| 8,286,845 B2 | 10/2012 | Perry et al. |
| 8,308,045 B2 | 11/2012 | Bettuchi et al. |
| 8,312,885 B2 | 11/2012 | Bettuchi et al. |
| 8,313,014 B2 | 11/2012 | Bettuchi |
| 8,317,073 B2 | 11/2012 | Milliman et al. |
| 8,317,074 B2 | 11/2012 | Ortiz et al. |
| 8,322,590 B2 | 12/2012 | Patel et al. |
| 8,328,060 B2 | 12/2012 | Jankowski et al. |
| 8,328,062 B2 | 12/2012 | Viola |
| 8,328,063 B2 | 12/2012 | Milliman et al. |
| 8,343,185 B2 | 1/2013 | Milliman et al. |
| 8,353,438 B2 | 1/2013 | Baxter, III et al. |
| 8,353,439 B2 | 1/2013 | Baxter, III et al. |
| 8,353,930 B2 | 1/2013 | Heinrich et al. |
| 8,360,295 B2 | 1/2013 | Milliman et al. |
| 8,365,974 B2 | 2/2013 | Milliman |
| 8,403,942 B2 | 3/2013 | Milliman et al. |
| 8,408,441 B2 | 4/2013 | Wenchell et al. |
| 8,413,870 B2 | 4/2013 | Pastorelli et al. |
| 8,413,872 B2 | 4/2013 | Patel |
| 8,418,905 B2 | 4/2013 | Milliman |
| 8,418,909 B2 | 4/2013 | Kostrzewski |
| 8,424,535 B2 | 4/2013 | Hessler et al. |
| 8,424,741 B2 | 4/2013 | McGuckin, Jr. et al. |
| 8,430,291 B2 | 4/2013 | Heinrich et al. |
| 8,430,292 B2 | 4/2013 | Patel et al. |
| 8,453,910 B2 | 6/2013 | Bettuchi et al. |
| 8,453,911 B2 | 6/2013 | Milliman et al. |
| 8,485,414 B2 | 7/2013 | Criscuolo et al. |
| 8,490,853 B2 | 7/2013 | Criscuolo et al. |
| 8,511,533 B2 | 8/2013 | Viola et al. |
| 8,551,138 B2 | 10/2013 | Orban, III et al. |
| 8,567,655 B2 | 10/2013 | Nalagatla et al. |
| 8,579,178 B2 | 11/2013 | Holsten et al. |
| 8,590,763 B2 | 11/2013 | Milliman |
| 8,590,764 B2 | 11/2013 | Hartwick et al. |
| 8,608,047 B2 | 12/2013 | Holsten et al. |
| 8,616,428 B2 | 12/2013 | Milliman et al. |
| 8,616,429 B2 | 12/2013 | Viola |
| 8,622,275 B2 | 1/2014 | Baxter, III et al. |
| 8,631,993 B2 | 1/2014 | Kostrzewski |
| 8,636,187 B2 | 1/2014 | Hueil et al. |
| 8,640,940 B2 | 2/2014 | Ohdaira |
| 8,662,370 B2 | 3/2014 | Takei |
| 8,663,258 B2 | 3/2014 | Bettuchi et al. |
| 8,672,931 B2 | 3/2014 | Goldboss et al. |
| 8,678,264 B2 | 3/2014 | Racenet et al. |
| 8,684,248 B2 | 4/2014 | Milliman |
| 8,684,250 B2 | 4/2014 | Bettuchi et al. |
| 8,684,251 B2 | 4/2014 | Rebuffat et al. |
| 8,684,252 B2 | 4/2014 | Patel et al. |
| 8,733,611 B2 | 5/2014 | Milliman |
| 2003/0111507 A1 | 6/2003 | Nunez |
| 2004/0073090 A1 | 4/2004 | Butler et al. |
| 2005/0051597 A1 | 3/2005 | Toledano |
| 2005/0107813 A1 | 5/2005 | Gilete Garcia |
| 2005/0205640 A1 * | 9/2005 | Milliman ............ A61B 17/1155 227/176.1 |
| 2006/0000869 A1 | 1/2006 | Fontayne |
| 2006/0011698 A1 | 1/2006 | Okada et al. |
| 2006/0201989 A1 | 9/2006 | Ojeda |
| 2007/0027473 A1 | 2/2007 | Vresh et al. |
| 2007/0029363 A1 | 2/2007 | Popov |
| 2007/0060952 A1 | 3/2007 | Roby et al. |
| 2008/0142566 A1 | 6/2008 | Gresham et al. |
| 2008/0228213 A1 * | 9/2008 | Blakeney ............ A61B 17/3421 606/185 |
| 2009/0173767 A1 | 7/2009 | Milliman |
| 2009/0236392 A1 | 9/2009 | Cole et al. |
| 2009/0236398 A1 | 9/2009 | Cole et al. |
| 2009/0236401 A1 | 9/2009 | Cole et al. |
| 2010/0019016 A1 | 1/2010 | Edoga et al. |
| 2010/0051668 A1 | 3/2010 | Milliman et al. |
| 2010/0084453 A1 | 4/2010 | Hu |
| 2010/0147923 A1 | 6/2010 | D'Agostino et al. |
| 2010/0163598 A1 | 7/2010 | Belzer |
| 2010/0224668 A1 | 9/2010 | Fontayne et al. |
| 2010/0230465 A1 | 9/2010 | Smith et al. |
| 2010/0258611 A1 | 10/2010 | Smith et al. |
| 2010/0264195 A1 | 10/2010 | Bettuchi |
| 2010/0327041 A1 | 12/2010 | Milliman et al. |
| 2011/0011916 A1 | 1/2011 | Levine |
| 2011/0114697 A1 | 5/2011 | Baxter, III et al. |
| 2011/0114700 A1 | 5/2011 | Baxter, III et al. |
| 2011/0139852 A1 | 6/2011 | Zingman |
| 2011/0144640 A1 | 6/2011 | Heinrich et al. |
| 2011/0147432 A1 | 6/2011 | Heinrich et al. |
| 2011/0192882 A1 | 8/2011 | Hess et al. |
| 2012/0145755 A1 | 6/2012 | Kahn |
| 2012/0193395 A1 | 8/2012 | Pastorelli et al. |
| 2012/0193398 A1 | 8/2012 | Williams et al. |
| 2012/0228356 A1 * | 9/2012 | Milliman ............ A61B 1/31 227/175.1 |
| 2012/0232339 A1 | 9/2012 | Csiky |
| 2012/0273548 A1 | 11/2012 | Ma et al. |
| 2012/0325888 A1 | 12/2012 | Qiao et al. |
| 2013/0015232 A1 | 1/2013 | Smith et al. |
| 2013/0020372 A1 | 1/2013 | Jankowski et al. |
| 2013/0020373 A1 | 1/2013 | Smith et al. |
| 2013/0032628 A1 | 2/2013 | Li et al. |
| 2013/0056516 A1 | 3/2013 | Viola |
| 2013/0060258 A1 | 3/2013 | Giacomantonio |
| 2013/0105544 A1 | 5/2013 | Mozdzierz et al. |
| 2013/0105546 A1 | 5/2013 | Milliman et al. |
| 2013/0105551 A1 | 5/2013 | Zingman |
| 2013/0126580 A1 | 5/2013 | Smith et al. |

(56) References Cited

U.S. PATENT DOCUMENTS

| | | |
|---|---|---|
| 2013/0153630 A1 | 6/2013 | Miller et al. |
| 2013/0153631 A1 | 6/2013 | Vasudevan et al. |
| 2013/0153633 A1 | 6/2013 | Casasanta, Jr. et al. |
| 2013/0153634 A1 | 6/2013 | Carter et al. |
| 2013/0153638 A1 | 6/2013 | Carter et al. |
| 2013/0153639 A1 | 6/2013 | Hodgkinson et al. |
| 2013/0175315 A1* | 7/2013 | Milliman ............ A61B 17/1155 227/175.1 |
| 2013/0175318 A1 | 7/2013 | Felder et al. |
| 2013/0175319 A1 | 7/2013 | Felder et al. |
| 2013/0175320 A1 | 7/2013 | Mandakolathur Vasudevan et al. |
| 2013/0181029 A1* | 7/2013 | Milliman ............. A61B 17/068 227/175.1 |
| 2013/0181035 A1 | 7/2013 | Milliman |
| 2013/0181036 A1 | 7/2013 | Olson et al. |
| 2013/0186930 A1 | 7/2013 | Wenchell et al. |
| 2013/0193185 A1 | 8/2013 | Patel |
| 2013/0193187 A1 | 8/2013 | Milliman |
| 2013/0193190 A1 | 8/2013 | Carter et al. |
| 2013/0193191 A1 | 8/2013 | Stevenson et al. |
| 2013/0193192 A1 | 8/2013 | Casasanta, Jr. et al. |
| 2013/0200131 A1 | 8/2013 | Racenet et al. |
| 2013/0206816 A1 | 8/2013 | Penna |
| 2013/0214027 A1 | 8/2013 | Hessler et al. |
| 2013/0214028 A1 | 8/2013 | Patel et al. |
| 2013/0228609 A1 | 9/2013 | Kostrzewski |
| 2013/0240597 A1 | 9/2013 | Milliman et al. |
| 2013/0240600 A1 | 9/2013 | Bettuchi |
| 2013/0248581 A1 | 9/2013 | Smith et al. |
| 2013/0277411 A1 | 10/2013 | Hodgkinson et al. |
| 2013/0277412 A1 | 10/2013 | Gresham et al. |
| 2013/0282052 A1* | 10/2013 | Aranyi ............. A61B 17/07207 606/208 |
| 2013/0284792 A1* | 10/2013 | Ma ........................... A61B 1/04 227/176.1 |
| 2013/0292449 A1 | 11/2013 | Bettuchi et al. |
| 2013/0299553 A1 | 11/2013 | Mozdzierz |
| 2013/0299554 A1 | 11/2013 | Mozdzierz |
| 2013/0306701 A1 | 11/2013 | Olson |
| 2013/0306707 A1 | 11/2013 | Viola et al. |
| 2013/0334279 A1* | 12/2013 | Prior .................... A61B 17/115 227/175.1 |
| 2014/0008413 A1 | 1/2014 | Williams |
| 2014/0012317 A1 | 1/2014 | Orban et al. |

FOREIGN PATENT DOCUMENTS

| | | |
|---|---|---|
| CN | 2764311 Y | 3/2006 |
| CN | 101647720 A | 2/2010 |
| CN | 201542673 U | 8/2010 |
| CN | 103251435 A | 8/2013 |
| DE | 1057729 B | 5/1959 |
| DE | 3301713 A1 | 7/1984 |
| EP | 0152382 A2 | 8/1985 |
| EP | 0173451 A1 | 3/1986 |
| EP | 0190022 A2 | 8/1986 |
| EP | 0282157 A1 | 9/1988 |
| EP | 0503689 A2 | 9/1992 |
| EP | 1354560 A2 | 10/2003 |
| EP | 2138118 A2 | 12/2009 |
| EP | 2168510 A1 | 3/2010 |
| EP | 2238926 A2 | 10/2010 |
| EP | 2524656 A2 | 11/2012 |
| FR | 1136020 A | 5/1957 |
| FR | 1461464 A | 2/1966 |
| FR | 1588250 A | 4/1970 |
| FR | 2443239 A1 | 7/1980 |
| GB | 1185292 A | 3/1970 |
| GB | 2016991 A | 9/1979 |
| GB | 2070499 A | 9/1981 |
| JP | 53-075675 | 6/1978 |
| JP | 54-156224 | 10/1979 |
| JP | 57-085938 | 5/1982 |
| JP | 61-160311 | 10/1986 |
| JP | 2004147969 A | 5/2004 |
| JP | 2013-138860 A | 7/2013 |
| NL | 7711347 A | 4/1979 |
| SU | 1049048 A1 | 10/1983 |
| SU | 1509052 A1 | 9/1989 |
| WO | 8706448 A1 | 11/1987 |
| WO | 8900406 A1 | 1/1989 |
| WO | 9006085 A1 | 6/1990 |
| WO | 98/35614 A1 | 8/1998 |
| WO | 2001/054594 A1 | 8/2001 |
| WO | 2008/107918 A1 | 9/2008 |
| WO | 2013090223 A1 | 6/2013 |

OTHER PUBLICATIONS

European Search Report dated Jan. 23, 2018, issued in EP Appln. No. 14894548.

Chinese Office Action dated Sep. 6, 2018, issued in CN Appln. No. 201480079696.

International Search Report for PCT/CN14/079738 date of completion is Feb. 27, 2015 (3 pages).

Chinese Office Action dated May 23, 2019, issued in CN Appln. No. 201480079696.

* cited by examiner

SURGICAL STAPLING APPARATUS

CROSS-REFERENCE TO RELATED APPLICATIONS

This application is a National Stage Application of PCT/CN14/079738 under 35USC § 371 (a), the disclosures of the above-identified application is hereby incorporated by reference in its entirety.

BACKGROUND

Technical Field

The present disclosure relates generally to a surgical stapling apparatus and, more particularly, to circular surgical stapling apparatus including structure to facilitate adjustment of a tissue gap defined between anvil and cartridge assemblies of the surgical stapling apparatus.

Background of Related Art

Circular stapling apparatuses are commonly used to join tubular tissue sections by circular anastomosis. Typically, circular stapling apparatus include an anvil assembly which is movable in relation to a staple head portion to clamp tissue. When the anvil assembly is fully approximated, the anvil assembly and staple head portion define a minimum tissue gap. Because the thickness of tissue sections to be joined will vary between patients and procedures, it may be desirable to provide an apparatus in which the minimum tissue gap can be easily adjusted.

SUMMARY

A surgical stapling apparatus in which the minimum tissue gap can be easily adjusted is provided. The apparatus includes a body portion, a head portion disposed on a distal end of the body portion supporting a plurality of staples, and an anvil assembly including an anvil. The anvil is movably supported in relation to the head portion between retracted and advanced positions. The anvil and the head portion define a minimum tissue gap in the retracted position. The apparatus further includes an approximation assembly extending through the body portion and the head portion. The approximation assembly has a distal end supporting the anvil assembly and actuable to move the anvil assembly relative to the head portion. The approximation assembly includes a screw extension secured to a drive screw. The screw extension and the drive screw are adapted to be secured together in at least first and second orientations. When in the first orientation the approximation assembly has a fixed first effective length and when in the second orientation, the approximation assembly has a fixed second effective length. The fixed first effective length is greater than the fixed second effective length. When in the first orientation, the anvil and the head portion define a first minimum tissue gap therebetween and when in the second orientation, the anvil and the head portion define a second minimum tissue gap therebetween.

In some embodiments, at least one of a distal end of the drive screw and a proximal end of the screw extension defines a first pair of openings and a second pair of openings, a central axis of the first pair of openings being longitudinally spaced from a central axis of the second pair of openings. The distance between the central axis of the first pair of openings and the central axis of the second pair of openings may be between 0.05 mm and 5 mm. The other of the distal end of the drive screw and the proximal end of the screw extension may define a throughbore configured to be selectively aligned with either of the first or second pair of openings. The throughbore may be aligned with the first pair of openings when the screw extension is in the first position and the throughbore may be aligned with the second pair of openings when the screw extension is in the second position. The central axis of the first pair of openings may be perpendicular to the central axis of the second pair of openings.

In embodiments, the plurality of staples measure 4.8 mm when the screw extension is in the first position and the plurality of staples measure 3.5 mm when the screw extension is in the second position. A distal end of the screw extension may include a retaining feature defining a plurality of slots. One of the plurality of slots may be disposed in a vertical position when the screw extension is in the first position. One of the plurality of slots may be disposed in a horizontal position when the screw extension is in the second position. The approximation assembly may further include an actuation knob coupled to the drive screw and selectively actuable to move the anvil assembly relative to the head portion. The handle portion may include a stationary handle and a firing trigger.

Also provided is a method of determining a minimum tissue gap of a surgical stapler. The method includes providing a surgical stapler having an anvil retainer and defining a longitudinal axis, a vertical axis, and a horizontal axis, the anvil retainer defining a plurality of slots in a distal end, viewing the distal end of the anvil retainer along the longitudinal axis of the surgical stapler, and identifying an orientation of the plurality of slots on the distal end of the anvil retainer relative to the vertical and horizontal axes, wherein the minimum tissue gap is a first distance when the plurality of slots are in a first orientation relative to the vertical and horizontal axes and the minimum tissue gap is second distance when the plurality of slots are in a second orientation relative to the vertical and horizontal axes.

BRIEF DESCRIPTION OF THE DRAWINGS

Various embodiments of the presently disclosed surgical stapling apparatus are described herein with reference to the drawings wherein.

DETAILED DESCRIPTION OF EMBODIMENTS

Embodiments of the presently disclosed surgical stapling apparatus will now be described in detail with reference to the drawings in which like reference numerals designate identical or corresponding elements in each of the several views. Throughout this description, the term "proximal" will refer to the portion of the apparatus closest to the user and the term "distal" will refer to the portion of the apparatus farthest from the user.

FIGS. 1-9B illustrate an embodiment of the presently disclosed surgical stapling apparatus designated generally by reference numeral 10. Surgical stapling apparatus 10 includes a proximal handle portion 20, an elongated central body portion 30, and a distal head portion 40. The length, shape and/or the diameter of proximal handle portion 20, central body portion 30, and/or distal head portion 40 may be selected to suit a particular surgical purpose or procedure. For example, central body portion 30 may be curved to facilitate access to a vessel lumen (not shown). Surgical stapling apparatus 10 further includes an anvil assembly 50 operably supported at the distal end of distal head portion 40 as will be described in further detail below.

Surgical stapling apparatus 10 and anvil assembly 50 will only be described to the extent necessary to fully disclose the aspects of the present disclosure. For a detailed description of the structure and function of an exemplary surgical stapling apparatus and anvil assembly, please refer to commonly owned U.S. Pat. No. 7,857,187 to Milliman ("the Milliman '187") and U.S. Pat. No. 6,945,444 to Gresham et al. ("the Gresham '444 patent"), the contents of which are incorporated by reference herein in their entireties.

Figure 1:
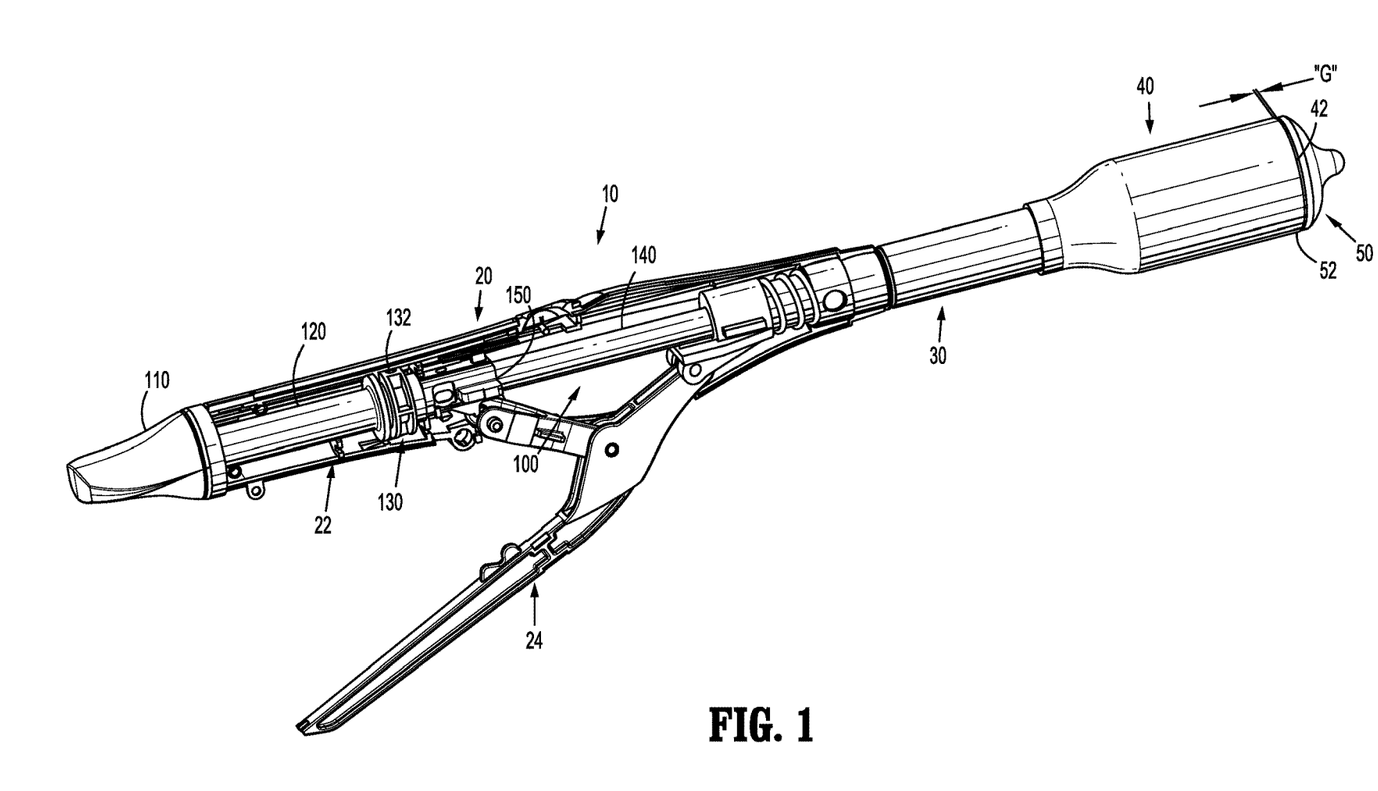
FIG. 1 is a perspective view of a surgical stapling apparatus according to the present disclosure with a housing half of a proximal handle portion removed.
Figure 2:
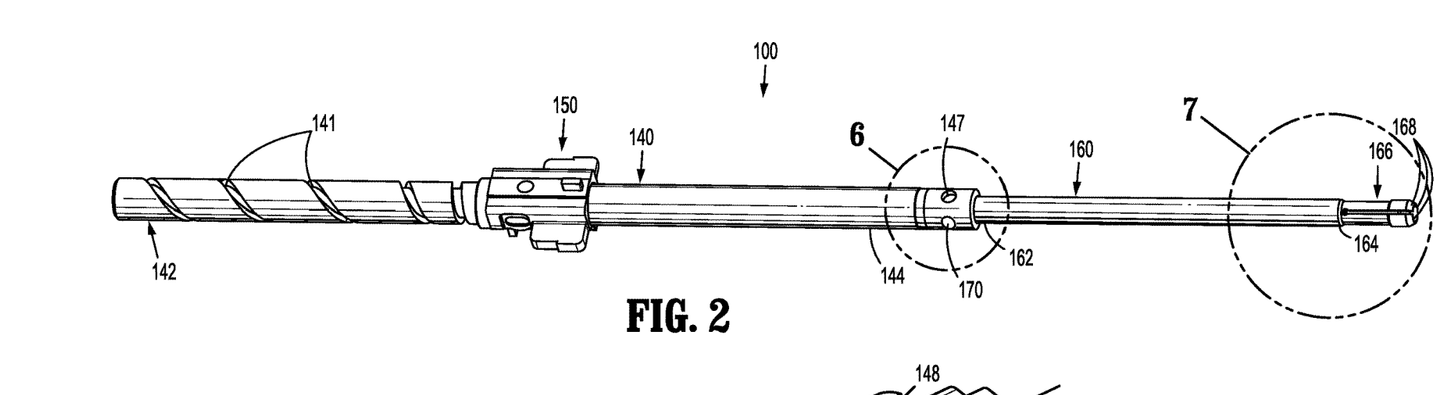
FIG. 2 is a perspective view of an approximation assembly of the surgical stapling apparatus shown in FIG. 1.

Referring to FIGS. 1 and 2, proximal handle portion 20 of surgical stapling apparatus 10 includes a stationary handle 22, a firing trigger 24, and an actuation knob 110. The actuation knob 110 is engaged with an approximation assembly 100 (FIG. 2) which extends from a proximal end of stationary handle 22 of the proximal handle portion 20 through central body portion 30 and to the distal head portion 40 of the surgical stapling apparatus 10. A distal end of the approximation assembly 100 supports the anvil assembly 50 adjacent the distal head portion 40. The approximation assembly 100 is operable to adjust the position of the anvil assembly 50 relative to distal head portion 40 of surgical stapling apparatus 10 between a fully approximated position and a fully advanced position. As will be described in further detail below, the configuration of approximation assembly 100 determines a "minimum tissue gap" "G," wherein the "minimum tissue gap" is the distance between an anvil head 52 of anvil assembly 50 and a staple holding component 42 of distal head portion 40 of surgical stapling apparatus 10 when approximation assembly 100 is fully approximated.

Approximation assembly 100 of surgical stapling apparatus 10 includes the actuation knob 110, a rotatable sleeve 120 secured to the actuation knob 110, a collar 130 secured to a distal end of the sleeve 120, a drive screw 140, a screw stop 150, and a screw extension 160. Rotatable sleeve 120 is rotatably received and axially fixed within stationary handle 22 of proximal handle portion 20 of surgical stapling apparatus 10. Drive screw 140 is received within rotatable sleeve 120 and is configured for longitudinal movement relative to rotatable sleeve 120 as actuation knob 110 is rotated. In particular, a pin 132 or other engagement feature is mounted within collar 130 and is received within a helical thread 141 (FIG. 2) defined on a proximal end 142 of drive screw 140. Rotation of actuation knob 110 causes rotation of rotatable sleeve 120 and collar 130. As collar 130 rotates, movement of pin 132 along helical thread 141 of drive screw 140 causes drive screw 140 to move longitudinally through collar 130. Rotation of actuation knob 110 in a first direction moves drive screw 140 in a distal direction, i.e., advances drive screw 140 relative to collar 130, and rotation of actuation knob 110 in a second direction moves drive screw 140 in a proximal direction, i.e., retracts drive screw 140 relative to collar 120.

Referring to FIG. 2, a proximal end 162 of screw extension 160 is secured to distal end 144 of drive screw 140 such that longitudinal movement of drive screw 140 causes corresponding longitudinal movement of screw extension 140. As will be described in further detail below, in one embodiment and as shown, screw extension 160 is fixedly secured to drive screw 140 by a pin 170. In an alternative embodiment, screw extension 160 may be fixedly secured to drive screw 140 with mechanical fasteners (not shown), a friction or snap fit arrangement, a tongue and groove configuration (not shown), or in any other suitable manner.

Figure 3:
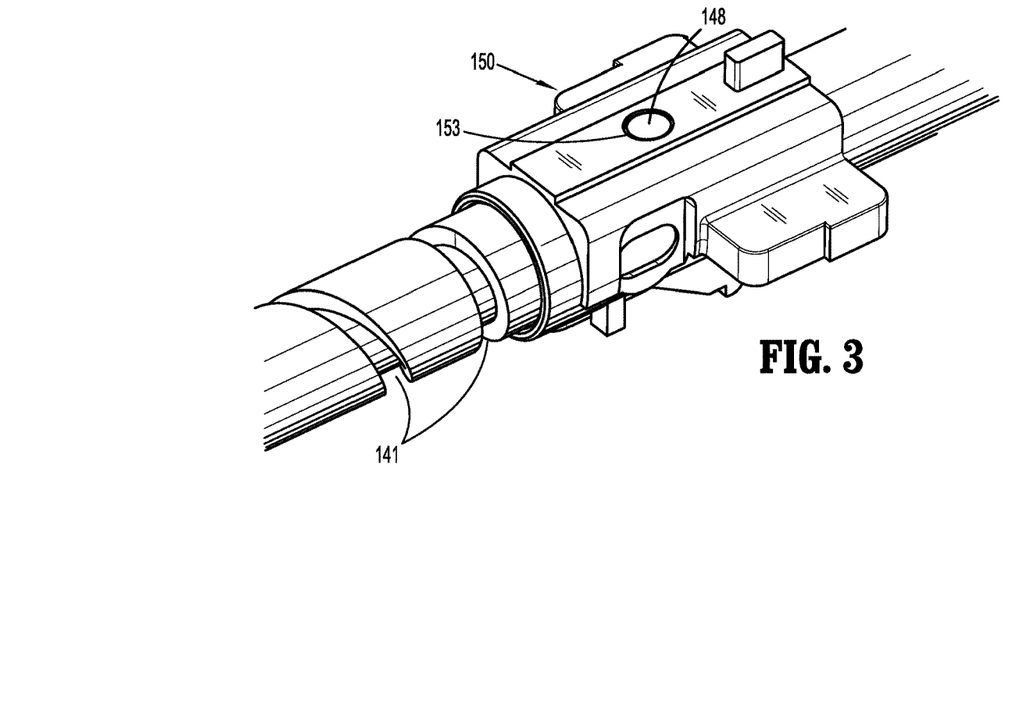
FIG. 3 is an enlarged perspective view of a drive screw, stop member, and connector pin of the approximation assembly shown in FIG. 2.
Figure 4:
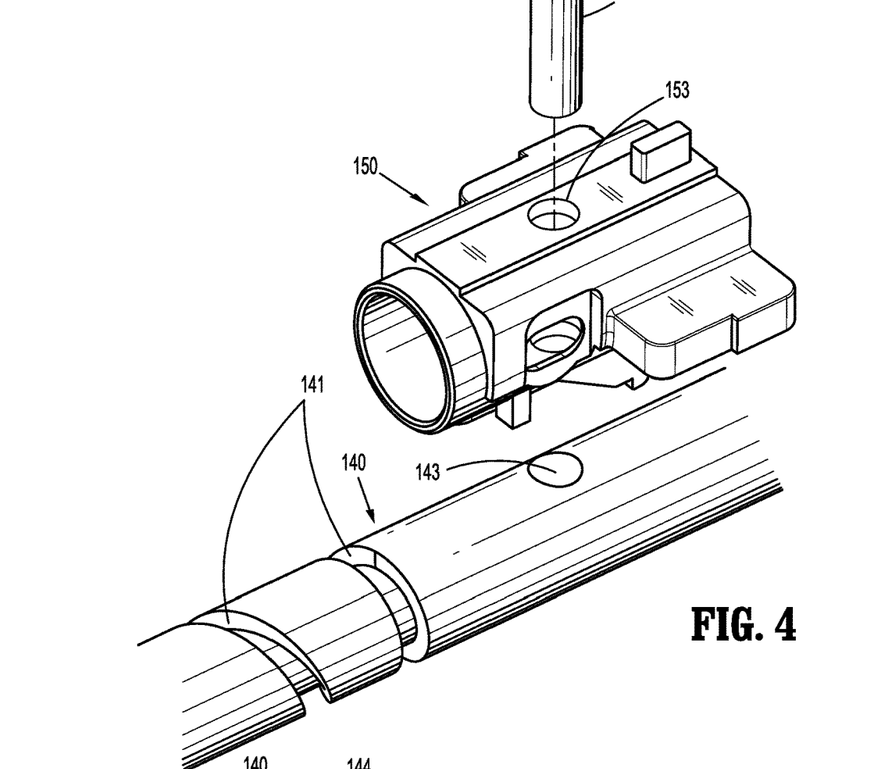
FIG. 4 is an exploded view of the drive screw, stop member, and connector pin shown in FIG. 3.

With reference to FIGS. 2-4, screw stop 150 is secured between proximal and distal ends 142, 144 of the drive screw 140 and distally of helical thread 141. A pin 148 is received through an opening 143 formed in drive screw 140 and an opening 153 in screw stop 150 to fixedly secure screw stop 150 onto drive screw 140. Screw stop 150 is positioned to engaged a stop surface (not shown) formed within the handle portion 20 to limit retraction of the drive screw 140 within the handle portion 20. The point at which the screw stop 150 engages the stop surface defines the fully approximated position of the anvil assembly 50 in relation to distal head portion 40. For a more detailed description of the operation of the screw stop 150, see, e.g., the Milliman '187 patent.

Figures 5, 6, 6A:
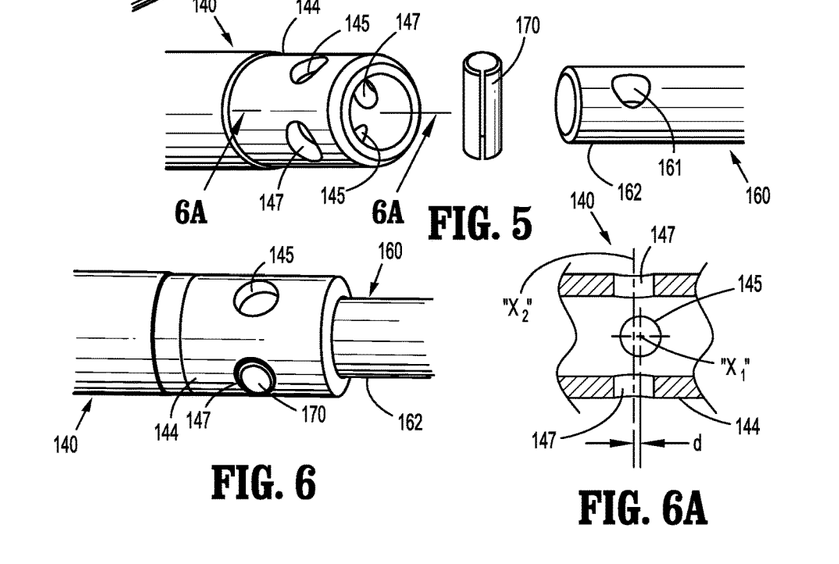
FIG. 5 is an exploded view of the distal end of the drive screw, the proximal end of the screw extension, and a pin of the approximation assembly shown in FIG. 2.
FIG. 6 is an enlarged view of the indicated area of detail shown in FIG. 2.
FIG. 6A is a cross-sectional view of the distal end of the drive screw taken along line 6A-6A shown in FIG. 5.

With reference to FIGS. 5 and 6, in one embodiment, and as shown, distal end 144 of drive screw 140 includes a first pair of opposed openings 145 and a second pair of opposed openings 147. Although shown having only two pair of opposed openings, it is envisioned that drive screw 140 may define more than two pair of opposed openings. A first central axis "x1" defined by the first pair of openings 145 is longitudinally spaced from a second central axis "x2" defined by the second pair of opposed opens 147 a distance "d". In one example, distance "d" between the first and second central axes "x1", "x2" of the respective first and second pairs of openings 145, 147 is 0.25 mm. Alternatively, the distance "d" may be between 0.05 mm to and 5 mm. Although first and second central axes "x1", "x2" are shown as being perpendicular to one another, it is envisioned that first and second central axes "x1", "x2" may be oriented or radially offset at any angle relative to each other.

Proximal end 162 of screw extension 160 defines a throughbore 161 which, in a first orientation is positioned to align with the first pair of openings 145 formed in the distal end 144 of drive screw 140 and, in the second orientation, is positioned to align with the second pair of openings 147 formed in the distal end 144 of drive screw 140. Screw extension 160 is secured to drive screw 140 with a pin 170 which is received through the throughbore 161 in screw extension 160 and through either of the first or second pair of openings 145, 147. In an alternative embodiment, screw extension 160 may include first and second pairs of openings (not shown) for selective orientation relative to a throughbore (not shown) in drive screw 140. In yet another embodiment, each of drive screw 140 and screw extension 160 may include first and second pairs of openings (not shown) for selective orientation relative to each other. In this manner, screw extension 160 may be secured to drive screw 140 in four (4) different orientations.

The effective length of the approximation assembly can be adjusted a distance of "d" by selectively securing the screw extension 160 to the drive screw 140 using the first or second pair of openings 145, 147 of drive screw 140. The effective length of drive screw 140 and screw extension 160, i.e., the approximation assembly, effects the position of the anvil assembly 50 in relation to the staple cartridge 42 when the anvil assembly 50 is fully retracted and, thus, determines the minimum tissue gap "G" (FIG. 1) of surgical stapling apparatus 10 (FIG. 1).

When the screw extension 160 is pinned to the drive screw 140 through the first pair of openings 145 in drive screw 160 the approximation assembly 100 has a fixed first effective length and the minimum tissue gap "G" (FIG. 1) defined between anvil 52 of anvil assembly 50 and staple cartridge 42 of distal head portion 40 of surgical stapling apparatus 10 having a first distance. When the screw extension 160 is pinned to the drive screw 140 through the second pair of openings 147 in drive screw 140, the approximation assembly 100 has a fixed second effective length and the minimum tissue gap "G" has a second distance. The difference between the first distance and the second distance is equal to distance "d" between first and second axes "x1", "x2" of the first and second pairs of openings 145, 147, respectively. In one embodiment, the first distance is selected for use with a surgical stapling apparatus 10 having 4.8 mm staples and the second distance is selected for use with a surgical stapling apparatus 10 having 3.5 mm staples.

Drive screw 140 and screw extension 160 can be secured together during the assembly process. The effective length of approximation assembly and thus, the resulting minimum tissue gap "G" of surgical stapling apparatus 10, can be selected prior to assembly of surgical stapling apparatus 10. Once the desired minimum tissue gap "G" is selected, the throughbore 161 in screw extension 160 can be aligned with one of the corresponding first or second pair of openings 145, 147 in drive screw 140 and pin 170 can be positioned through the throughbore 161 and the selected pair of openings 145, 147. As discussed above, in one embodiment, alignment of the throughbore 161 in screw extension 160 with the first pair of openings 145 of drive screw 140 results in a tissue gap "G" that is 0.25 mm greater than the tissue gap which results from aligning throughbore 161 of screw extension 160 with the second pair of openings 147. In this manner, the minimum tissue gap "G" of surgical stapling apparatus 10 can be adjusted during assembly of surgical stapling apparatus 10 simply by aligning the throughbore 161 in screw extension 160 with the other of the first and second pair of openings 145, 147. Thus, the adjustment of the minimum tissue gap "G" requires no modification to the existing structures of the surgical stapling apparatus 10 and no additional structure.

Figure 7:
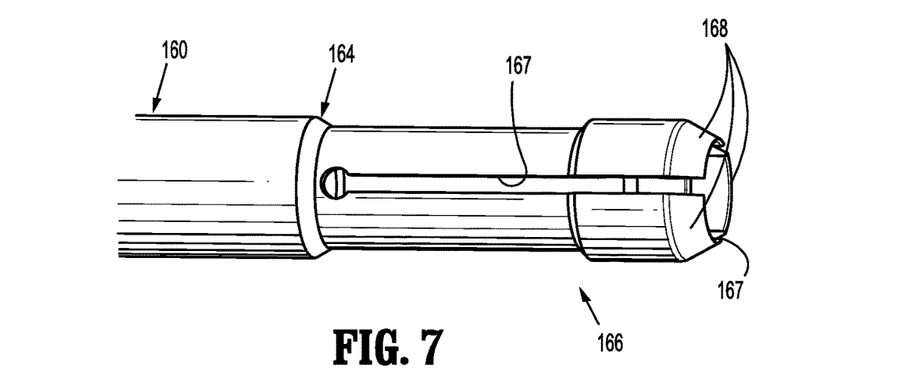
FIG. 7 is an enlarged view of the indicated area of detail shown in FIG. 2.

With reference now to FIG. 7, distal end 164 of screw extension 160 includes anvil retainer 166. Anvil retainer 166 includes a plurality of arms 168 configured to selectively engage an anvil center rod (not shown) of anvil assembly 50 (FIG. 1). As shown, anvil retainer 166 includes three (3) arms 168 in an annular configuration for selectively receiving the anvil center rod (not shown) of anvil assembly 50 (FIG. 1). Arms 168 define equally spaced slots 167 therebetween. The orientation of slots 167 of anvil retainer 166 when secured to the distal end 164 of screw extension 160 allow a user to visually identify which of the first or second pair of openings 145, 147 in drive screw 140 are aligned with the throughbore 161 in screw extension 160, and thus, identify the selected minimum tissue gap "G" of surgical stapling apparatus 10 as described in detail below.

Figure 8A:
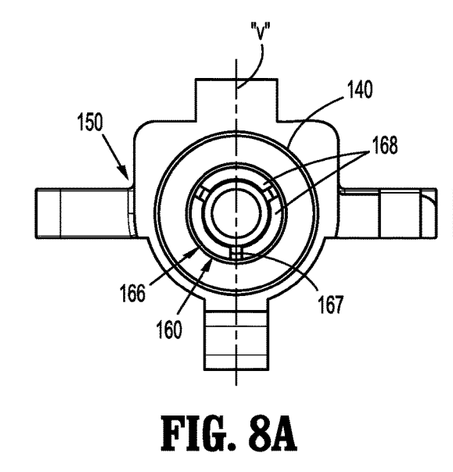
FIG. 8A is a distal end view of the approximation assembly of FIG. 2 with the screw extension in a first position.
Figure 8B:
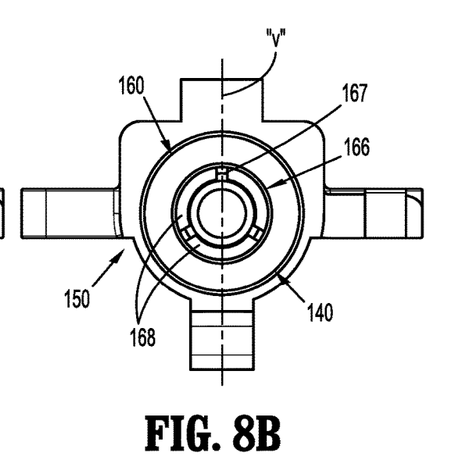
FIG. 8B is a distal end view of the approximation assembly shown in FIG. 2 with the screw extension rotated 180° about its longitudinal axis.

FIGS. 8A and 8B show a distal end view of approximation assembly 100 of surgical stapling apparatus 10 (FIG. 1) wherein the screw extension 160 is in the first position, i.e., with the throughbore 161 (FIG. 6) of screw extension 160 aligned with pair of first openings 145 (FIG. 6) of drive screw 140. When the throughbore 161 in screw extension 160 is aligned with the first pair of openings 145, one of slots 167 in retaining feature 166 of screw extension 160 is in a vertical position relative to approximation assembly 100, as indicated by vertical axis "v" shown in FIGS. 8A and 8B. The vertical positioning of slot 167 may be on the bottom (FIG. 8A) of retaining feature 166 or on the top (FIG. 8B) of retaining feature 166.

Figure 9A:
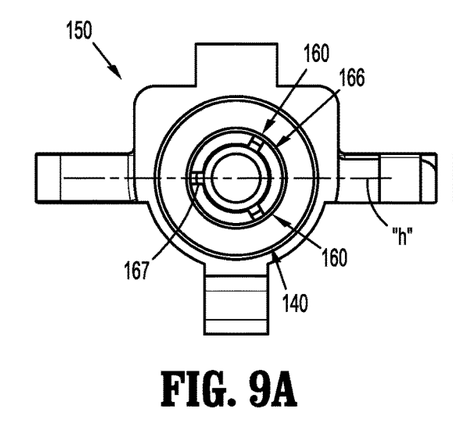
FIG. 9A is a distal end view of the approximation assembly shown in FIG. 2 in a second position.
Figure 9B:
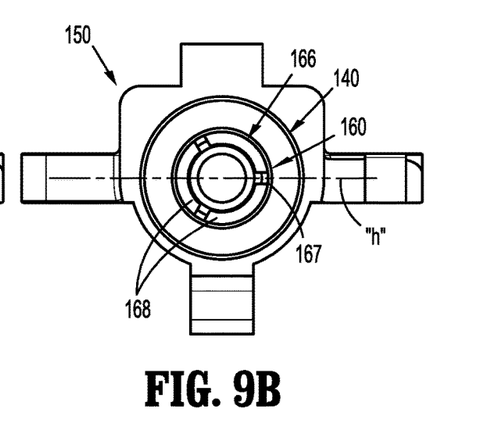
FIG. 9B is a distal end view of the approximation assembly shown in FIG. 2 with the screw extension rotated 180° about its longitudinal axis.

FIGS. 9A and 9B show a distal end view of approximation assembly 100 of surgical stapling apparatus 10 (FIG. 1) wherein the screw extension 160 is in the second position, i.e., with the throughbore 161 of screw extension 160 aligned with the pair of second openings 147 (FIG. 6) of drive screw 140. When the throughbore 161 in screw extension 160 is aligned with the second pair of openings 147, one of slots 167 in retaining feature 166 of screw extension 160 is in a horizontal position relative to approximation assembly 100, as indicated by horizontal axis "h" shown in FIGS. 9A and 9B. The horizontal positioning of slots 167 may be on the left (FIG. 9A) of retaining feature 166 or on the right (FIG. 9B) of retaining feature 166.

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the disclosure based on the above-described embodiments. Accordingly, the disclosure is not to be limited by what has been particularly shown and described, except as indicated by the appended claims. For example, as discussed above, multiple pairs of openings which are angularly offset and longitudinally spaced may be provided on either the screw extension 160 and/or the drive screw 140 to facilitate greater selectively of adjustment of the minimum tissue gap of the stapling apparatus. Further the throughbore 161 can be provided on the screw extension 160 and/or the drive screw 140, and may only extend partially through the component.

What is claimed is:
1. A surgical stapling apparatus comprising:
a body portion;
a head portion disposed on a distal end of the body portion, the head portion supporting a plurality of staples;
an anvil assembly including an anvil, the anvil being movably supported in relation to the head portion between retracted and advanced positions, the anvil and the head portion defining a minimum tissue gap in the retracted position;

an approximation assembly extending through the body portion and the head portion, the approximation assembly having a distal end supporting the anvil assembly and being actuable to move the anvil assembly relative to the head portion, the approximation assembly including a screw extension secured to a drive screw, the screw extension and the drive screw being adapted to be secured together in at least first and second rotational orientations, wherein in the first rotational orientation the approximation assembly has a fixed first effective length and in the second rotational orientation the approximation assembly has a fixed second effective length, wherein the fixed first effective length is greater than the fixed second effective length, wherein in the first rotational orientation, the anvil and the head portion define a first minimum tissue gap therebetween and in the second rotational orientation, the anvil and the head portion define a second minimum tissue gap therebetween.

2. The surgical stapling apparatus according to claim 1, wherein at least one of a distal end of the drive screw and a proximal end of the screw extension defines a first pair of openings and a second pair of openings, a central axis of the first pair of openings being longitudinally spaced from a central axis of the second pair of openings.

3. The surgical stapling apparatus according to claim 2, wherein the distance between the central axis of the first pair of openings and the central axis of the second pair of openings is between 0.05 mm and 5 mm.

4. The surgical stapling apparatus according to claim 2, wherein the other of the distal end of the drive screw and the proximal end of the screw extension defines a throughbore configured to be selectively aligned with either of the first or second pair of openings.

5. The surgical stapling apparatus according to claim 4, wherein the throughbore is aligned with the first pair of openings when the screw extension is in the first position and the throughbore is aligned with the second pair of openings when the screw extension is in the second position.

6. The surgical stapling apparatus according to claim 1, wherein the plurality of staples measure 4.8 mm when the screw extension is in the first position and the plurality of staples measure 3.5 mm when the screw extension is in the second position.

7. The surgical stapling apparatus according to claim 2, wherein the central axis of the first pair of openings is perpendicular to the central axis of the second pair of openings.

8. The surgical stapling apparatus according to claim 1, wherein a distal end of the screw extension includes a retaining feature defining a plurality of slots.

9. The surgical stapling apparatus according to claim 8, wherein one of the plurality of slots is disposed in a vertical position when the screw extension is in the first position.

10. The surgical stapling apparatus according to claim 9, wherein one of the plurality of slots is disposed in a horizontal position when the screw extension is in the second position.

11. The surgical stapling apparatus according to claim 1, wherein the approximation assembly further includes an actuation knob coupled to the drive screw and selectively actuable to move the anvil assembly relative to the head portion.

12. The surgical stapling apparatus according to claim 1, further including a handle portion disposed on a proximal end of the body portion, wherein the handle portion includes a stationary handle and a firing trigger.

13. A surgical stapling apparatus comprising:
a body portion;
a head portion disposed on a distal end of the body portion, the head portion supporting a plurality of staples;
an anvil assembly including an anvil, the anvil being movably supported in relation to the head portion between retracted and advanced positions, the anvil and the head portion defining a minimum tissue gap in the retracted position;
an approximation assembly extending through the body portion and the head portion, the approximation assembly having a distal end supporting the anvil assembly and being actuable to move the anvil assembly relative to the head portion, the approximation assembly including a screw extension secured to a drive screw defining a helical thread, the screw extension and the drive screw being adapted to be secured together in at least first and second orientations, wherein in the first orientation, the approximation assembly has a fixed first effective length and in the second orientation, the approximation assembly has a fixed second effective length, wherein the fixed first effective length is greater than the fixed second effective length, wherein in the first orientation, the anvil and the head portion define a first minimum tissue gap therebetween and in the second orientation, the anvil and the head portion define a second minimum tissue gap therebetween.

14. The surgical stapling apparatus according to claim 13, wherein at least one of a distal end of the drive screw and a proximal end of the screw extension defines a first pair of openings and a second pair of openings, a central axis of the first pair of openings being longitudinally spaced from a central axis of the second pair of openings.

15. The surgical stapling apparatus according to claim 13, wherein the other of the distal end of the drive screw and the proximal end of the screw extension defines a throughbore configured to be selectively aligned with either of the first or second pair of openings.

16. The surgical stapling apparatus according to claim 15, wherein the throughbore is aligned with the first pair of openings when the screw extension is in the first position and the throughbore is aligned with the second pair of openings when the screw extension is in the second position.

17. A surgical stapling apparatus comprising:
a body portion;
a head portion disposed on a distal end of the body portion, the head portion supporting a plurality of staples;
an anvil assembly including an anvil, the anvil being movably supported in relation to the head portion between retracted and advanced positions, the anvil and the head portion defining a minimum tissue gap in the retracted position;
an approximation assembly extending through the body portion and the head portion, the approximation assembly having a distal end supporting the anvil assembly and being actuable to move the anvil assembly relative to the head portion, the approximation assembly including a screw extension secured to a drive screw and a rotatable sleeve received about the drive screw, the screw extension and the drive screw being adapted to be secured together in at least first and second orientations, wherein in the first orientation, the approximation assembly has a fixed first effective length and in the second orientation, the approximation assembly has a fixed second effective length, wherein the fixed first effective length is greater than the fixed second effective length, wherein in the first orientation, the anvil and the head portion define a first minimum tissue gap therebetween and in the second orientation, the anvil and the head portion define a second minimum tissue gap therebetween.

18. The surgical stapling apparatus according to claim 17, wherein at least one of a distal end of the drive screw and a proximal end of the screw extension defines a first pair of openings and a second pair of openings, a central axis of the first pair of openings being longitudinally spaced from a central axis of the second pair of openings.

19. The surgical stapling apparatus according to claim 17, wherein the other of the distal end of the drive screw and the proximal end of the screw extension defines a throughbore configured to be selectively aligned with either of the first or second pair of openings.

20. The surgical stapling apparatus according to claim 19, wherein the throughbore is aligned with the first pair of openings when the screw extension is in the first position and the throughbore is aligned with the second pair of openings when the screw extension is in the second position.

* * * * *